United States Patent [19]

Capozzi et al.

[11] Patent Number: 5,116,315
[45] Date of Patent: * May 26, 1992

[54] BIOLOGICAL SYRINGE SYSTEM

[75] Inventors: Emil E. Capozzi, Costa Mesa; H. Stephen Cooksten, Malibu, both of Calif.

[73] Assignee: Hemaedics, Inc., Malibu, Calif.

[*] Notice: The portion of the term of this patent subsequent to Dec. 18, 2007 has been disclaimed.

[21] Appl. No.: 459,134

[22] Filed: Dec. 29, 1989

Related U.S. Application Data

[63] Continuation-in-part of Ser. No. 418,707, Oct. 3, 1989, Pat. No. 4,978,336, which is a continuation of Ser. No. 102,543, Sep. 29, 1987, abandoned.

[51] Int. Cl.$^5$ ............................................. A01M 37/00
[52] U.S. Cl. ..................................... 604/82; 604/191; 222/137; 235/398; 235/432
[58] Field of Search ............... 604/82, 83, 94, 191, 604/240, 242, 243, 283, 905; 239/398, 432; 600/4, 5; 222/137, 129, 145

[56] References Cited

U.S. PATENT DOCUMENTS

| | | | |
|---|---|---|---|
| 2,158,593 | 5/1939 | Scrimgeour | 604/242 |
| 3,179,107 | 4/1965 | Clark | 604/242 |
| 4,040,420 | 8/1977 | Speer | 609/272 X |
| 4,109,653 | 8/1978 | Kozan | 604/191 |
| 4,359,049 | 11/1982 | Redl et al. | 604/191 |
| 4,629,455 | 12/1986 | Kanno | 604/905 |
| 4,631,055 | 12/1986 | Redl et al. | 604/191 |
| 4,735,616 | 4/1988 | Eibl et al. | 604/191 |
| 4,743,229 | 5/1988 | Chu | 604/82 |
| 4,842,581 | 6/1989 | Davis | 604/38 |
| 4,874,368 | 10/1989 | Miller et al. | 604/82 |
| 4,978,336 | 12/1990 | Capozzi et al. | 604/82 |
| 4,979,942 | 12/1990 | Wolf et al. | 604/83 |
| 5,049,135 | 9/1991 | Davis | 604/181 |

*Primary Examiner*—C. Fred Rosenbaum
*Assistant Examiner*—Mark O. Polutta
*Attorney, Agent, or Firm*—Daniel L. Dawes

[57] ABSTRACT

A biological syringe system for delivering a first and second fluid in a mixed composition comprising a manifold. The manifold has first and second component channels therethrough and first and second input connections respectively communicating with the first and second component channels. The first and second component channels terminate in exit channels adjacent to each other on an opposing end of the manifold. A discharge assembly is coupled to the opposing end of the manifold and receives fluid from both of the exit channels. The discharge assembly is used for mixing fluid from both of the exit channels and delivering the mixed fluid in a spray. The discharge assembly has a first and second passage therethrough communicating with the exit channels from the manifold for carrying fluid from the first and second component channels in corresponding first and second passages within the discharge assembly while maintaining the first and second fluids separated from each other. The discharge assembly has a mixing space defined therein to receive separate flows from the passages. The discharge assembly further comprises a mixing mechanism disposed within the mixing space to thoroughly mix the first and second fluids for the first time within the mixing space and to immediately thereafter atomize the thoroughly mixed first and second fluids in a spray discharged from the discharge assembly.

19 Claims, 4 Drawing Sheets

BIOLOGICAL SYRINGE SYSTEM

This is a continuation-in-part of U.S. Ser. No. 07/418,707 filed Oct. 3, 1989 now U.S. Pat. No. 4,978,336, which is a continuation of U.S. Ser. No. 07/102,543 filed Sep. 29, 1987, now abandoned.

FIELD OF THE INVENTION

This invention is directed to a biological syringe system wherein two syringes separately deliver proteins which form a tissue adhesive, and wherein a manifold locks onto the syringes and a needle locks onto the manifold to deliver the mixed proteins to promote coagulation and healing.

BACKGROUND OF THE INVENTION

A biological tissue adhesive is formed when a water solution containing blood factor XIII and fibrinogen is mixed with a water solution containing thrombin. The rate at which the adhesive sets or hardens principally depends upon the thrombin concentration. The mixture is applied to the laceration site which is to be adhered or protected. Previous methods of application included applying one solution to the site of adhesion and then applying the other solution thereto. The disadvantage of this method is that inadequate mixing occurs at the site to result in setting of the adhesive at the interface between the two solutions, without good adhesion to the adjacent biological surfaces.

Another method of application comprises the premixing of the two solutions in a mixing vessel, whereupon it is drawn into a syringe and then applied to the site to be adhered. This method requires promptness of application since the setting of the adhesive starts when the two solutions are combined. The time from mixing to the time of application to the site must be quite short, and depends upon the concentration of the thrombin solution.

In another method of application, two syringes are clamped together and the output cones are inserted into a Y-piece. When the mixing occurs in the Y-piece, the adhesive setting also occurs therein to plug it up. When the mixing occurs in the needle connected onto the Y-piece, plug-up of the needle causes buildup of pressure in the Y-piece so that the needle may be separated and injected into the field, possibly into the patient. Thus, there is need for a biological syringe system wherein the needle and other parts cannot become inadvertently detached so that no parts are ejected.

BRIEF SUMMARY OF THE INVENTION

The invention is a biological syringe system for delivering a first and second fluid in a mixed composition comprising a manifold. The manifold has first and second component channels therethrough and first and second input connections respectively communicating with the first and second component channels. The first and second component channels terminate in exit channels adjacent to each other on an opposing end of the manifold. A discharge assembly is coupled to the opposing end of the manifold and receives fluid from both of the exit channels. The discharge assembly is used for mixing fluid from both of the exit channels and delivering the mixed fluid in a spray. The discharge assembly has a first and second passage therethrough communicating with the exit channels from the manifold for carrying fluid from the first and second component channels in corresponding first and second passages within the discharge assembly while maintaining the first and second fluids separated from each other. The discharge assembly has a mixing space defined therein to receive separate flows from the passages. The discharge assembly further comprises a mixing mechanism disposed within the mixing space to thoroughly mix the first and second fluids for the first time within the mixing space and to immediately thereafter atomize the thoroughly mixed first and second fluids in a spray discharged from the discharge assembly.

The mechanism for thoroughly mixing and atomizing the first and second fluid into a spray comprises a shaped spray nozzle having a spray outlet defined therein. The shaped spray nozzle is disposed within the mixing space.

The first and second passages have outlet ends. The discharge assembly comprises a solid cylindrical body disposed within the mixing space. The solid cylindrical body having a first end surface adjacent outlet ends of first and second passage in the discharge assembly. The first and second fluids exit the outlet ends of the passages and flow into a cylindrical annular space between the nozzle disposed in the mixing space and the cylindrical body disposed in the mixing space. The first and second fluids mix for the first time within the cylindrical annular space and flow to a portion of the mixing space adjacent an opposing end of the solid cylindrical body opposite the spray outlet. The mixed first and second fluids then are expressed through the spray outlet as atomized spray particles.

The mechanism swirls the first and second fluids together in the mixing space. The mechanism comprises a plurality of wedged shaped surfaces azimuthally disposed about the spray outlet. The wedged shaped surfaces are inclined in an azimuthal direction relative to the spray outlet to impel an azimuthal flow to the first and second fluids about the spray outlet.

A channel separates each of the wedged shaped surfaces. The channel in combination with an adjacent wedged shaped surface directs the flow of the first and second fluid in an azimuthal direction about a predetermined cylindrical space adjacent to and centered about the spray outlet.

The mechanism spirals the first and second fluids together to thoroughly mix the first and second fluids for the first time immediately prior to ejection through the spray outlet.

The invention is also a method for applying a tissue adhesive and protective covering which chemically forms and hardens as applied comprising the steps of providing a first fluid, and providing a second fluid which when mixed with the first fluid hardens into the tissue adhesive. The first and second fluids are forced from a corresponding first and second syringe into corresponding first and second passages. The first and second fluids are partially mixed together by flowing the fluids under pressure within a cylindrical annular space. The partially mixed first and second fluids are forced from the cylindrical annular space into a final mixing chamber. The first and second fluids are then thoroughly mixed in the final mixing chamber. The thoroughly mixed fluids are forced into an axial spray orifice. The thoroughly mixed first and second fluids are atomized by pressured ejection of the fluids through the spray orifice at a predetermined minimum pressure.

As a result, mixture of the first and second fluids is substantially improved. strength and hardening of the tissue adhesive substantially improved, and wherein thorough mixing occurs just prior to application in atomized form.

In the method the first and second fluids are swirled together as the first and second fluid flows from the outlet ends of the passages through the cylindrical annular space and thence radially inward to an axial spray orifice to thoroughly mix the fluids within a mixing space of predetermined limited volume followed by immediate ejection in atomized form for application and hardening.

In the step of thoroughly mixing the first and second fluids, the first and second fluids are spiralled together for the first time just prior to forcing the fluids through the spray outlet.

The invention is further characterized as a method for applying a tissue adhesive and protective covering which chemically forms and hardens as applied comprising the steps of providing a first fluid, and separately providing a second fluid which when mixed with the first fluid hardens into the tissue adhesive. The first and second fluids are maintained substantially separate as the fluids are delivered to a mixing chamber. The first and second fluids are thoroughly mixed in the mixing chamber for the first time. The thoroughly mixed first and second fluids are immediately atomized by pressured ejection of the fluids through a spray orifice at a predetermined minimum pressure. The step of thoroughly mixing is performed immediately before the step of atomizing so that substantially no reaction has occurred between the first and second fluids until after the step of atomizing.

As a result, mixture of the first and second fluids is substantially improved, strength and hardening of the tissue adhesive substantially improved, and wherein thorough mixing occurs just prior to application in atomized form.

The step of thoroughly mixing the first and second fluids comprises the step of swirling the first and second fluids together for the first time in the mixing chamber just prior to atomizing.

The step of thoroughly mixing is performed relative to the other steps of the method to minimize the time during which the first and second fluids are is are mixed together.

The method further comprises the step of uniformly applying the atomized mixture of the first and second fluids to a selected wound site.

The method further comprises the step of curing the applied mixture of the first and second fluids to form an artificial tissue surface.

The step of curing is performed to minimize the time during which curing of the artificial tissue occurs after the step of atomizing.

Turn now to the drawings wherein like elements are referenced by like numerals and wherein the invention can better be visualized.

DESCRIPTION OF THE PREFERRED EMBODIMENT

Figures 1, 5, 6:
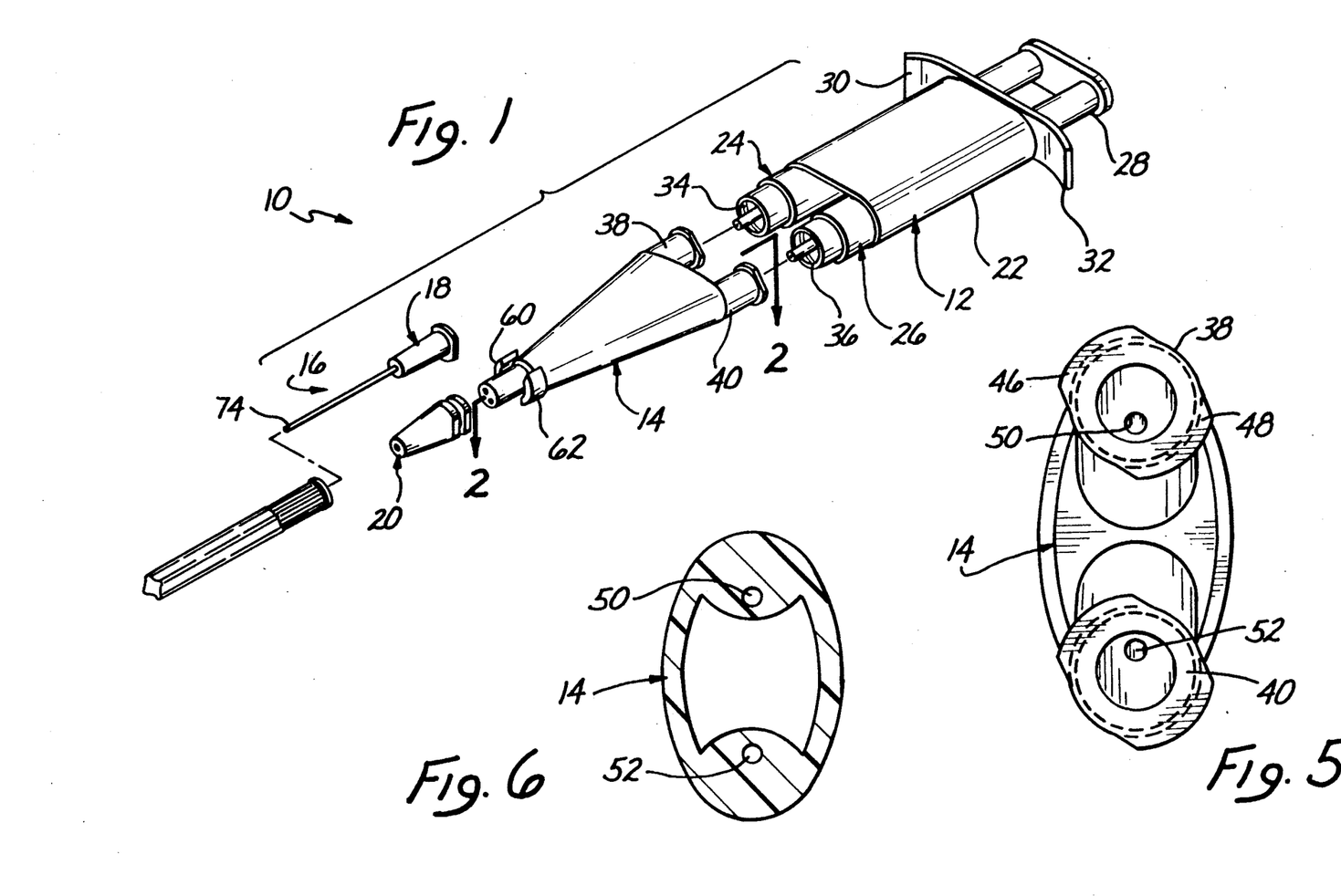
FIG. 1 is an exploded perspective view of the biological syringe system of this invention.
FIG. 5 is an end view of the manifold, as seen generally along the line 5—5 of FIG. 2.
FIG. 6 is a section through the manifold, as seen generally along the line 6—6 of FIG. 2.

The biological syringe system of this invention is generally indicated at 10 in FIG. 1. The syringe system comprises a syringe holder 12, manifold 14 and adhesive applicator 16. The adhesive applicator 16 is generally indicated in FIG. 1 because it may be either a needle assembly 18 or a spray assembly 20. The manifold 14 is shown in more detail in FIGS. 2, 5, 6 and 7. The needle assembly is shown in more detail in FIG. 2, and the spray assembly is shown in more detail in FIGS. 2, 4 and 8.

The syringe holder 12, as seen in FIG. 1, has a channel-shaped body 22 which is open on the bottom, as seen in FIG. 1, to detachably receive two syringes 24 and 26. Cap 28 engages the plungers of both syringes so that the plungers are depressed at the same time and speed. Flanges 30 and 32 permit one-handed grasp of the syringe holder, in the fingers so that the user's thumb can depress the syringe plungers together. Syringes 24 and 26 are respectively fitted at their forward ends with lock fittings 34 and 36. These lock fittings are suitable to detachably lock together with companion fittings on manifold 14. Lock fitting 36 is shown in dashed lines in FIG. 2.

Manifold 14 is configured to detachably lock to the syringes and bring the output streams thereof close together. Manifold 14 is in the form of a conical ellipsoid which has lock fittings 38 and 40 at its right end. These lock fittings respectively have conical seal joints 42 and 44 thereon to receive the conical nose on their respective syringes and seal with respect thereto. Lock fittings 38 and 40, see FIG. 5, each have a pair of ears extending from the otherwise generally cylindrical exterior surface. Ears 46 and 48 are shown with respect to fitting 38. The nose of the syringe has exterior of its conical nose a cylindrical sleeve which extends over the ears 46 and 48 and has inclined flanges which engage under the ears 46 and 48 so that when inserted, a quarter turn locks the fitting together. The structure of the nose of the syringe will be described in more detail with respect to the small end of the manifold.

Figure 2:
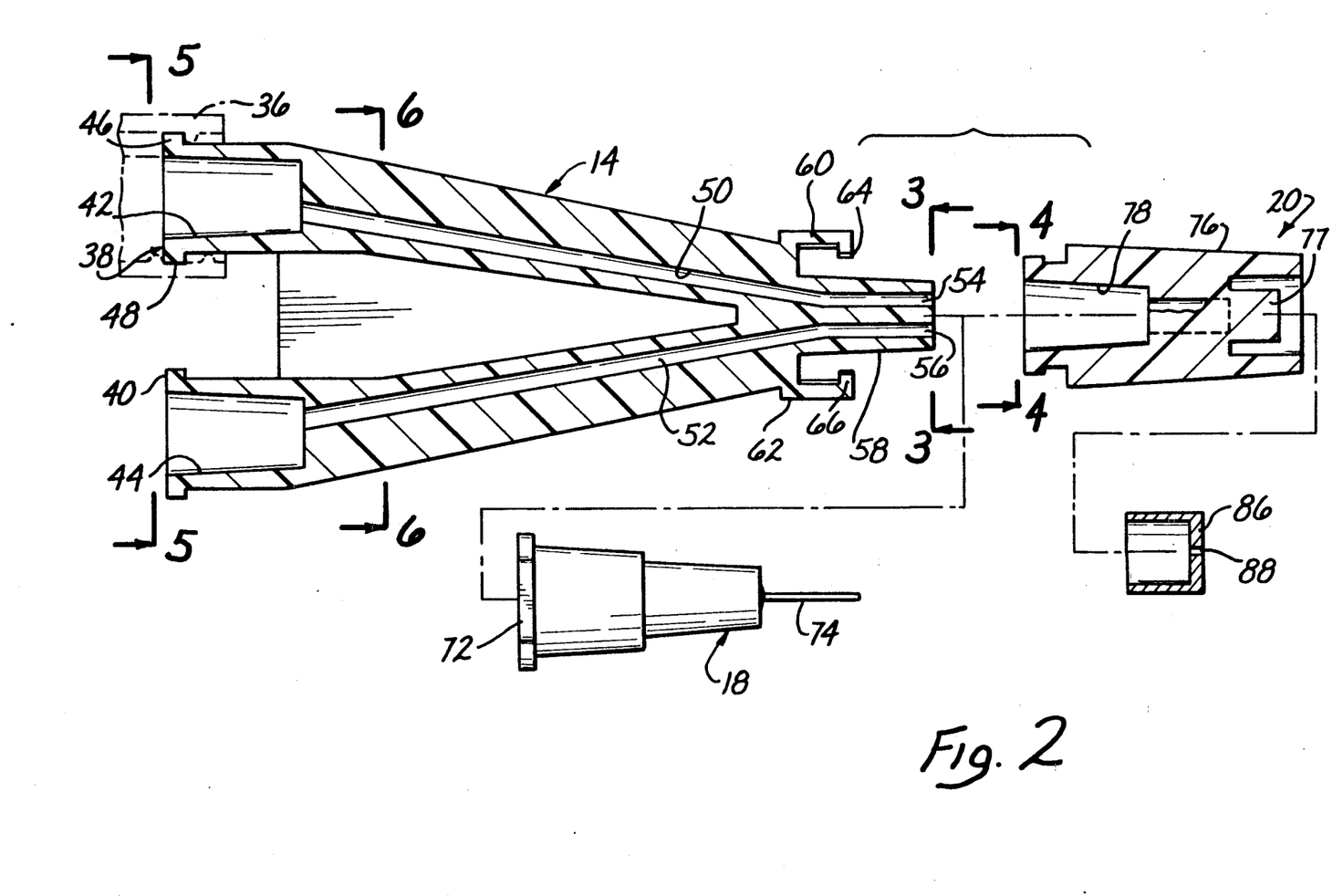
FIG. 2 is an enlarged section through the manifold thereof, as seen generally along the line 2—2 of FIG. 1.
Figure 3:
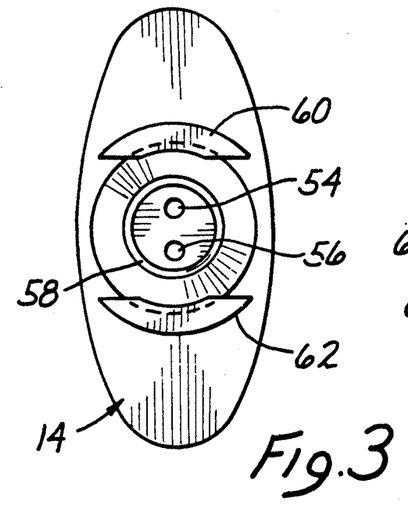
FIG. 3 is an end view of the manifold, as seen generally along the line 3—3 of FIG. 2.

Component channels 50 and 52 extend separately through the manifold from the conical recesses 42 and 44 which receive the noses of the syringes to the right end of the manifold, as seen in FIG. 2. At the right end, they form separate exit channels 54 and 56 in the truncated conical forward nose 58 of the manifold. The conical nose is the same size as the conical cone on each syringe. A collar surrounds the conical nose, but the collar is interrupted to form collar segments 60 and 62, particularly see FIG. 3. The respective collar segments 60 and 62 carry flanges 64 and 66 which have an angular inner surface in the axial direction towards the larger end of the cone. The collar segments and flanges are sized so that the ears 68 and 70 on spray assembly 20, see FIG. 4, and the corresponding ears on needle 18, with ear 72 shown in FIG. 2, fit between the collar segment when ears are correctly oriented and lock behind the collar segments when the spray assembly or needle assembly is rotated a quarter turn in the clockwise direction, as looking axially towards the larger end of the conical nose.

Figure 7:
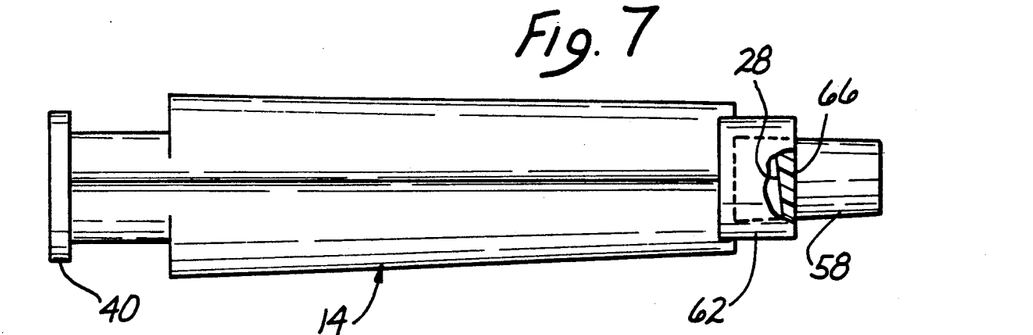
FIG. 7 is an edge view of the manifold, with parts broken away and parts taken in section.

Needle assembly 18 is configured to receive the conical nose 58 and have its ears, including ear 72, pass between the flanges 64 and 66, and upon rotation, the ears lock behind the flanges to hold the needle assembly in place. The needle assembly has a large enough interior passage to receive outflow from both exit channels 54 and 56, and this outflow passes through needle 74 and is mixed therein so that at the needle tip, mixed adhesive is delivered. FIG. 7 shows the collar segment 62 broken away to expose flange 66 and show its angular locking surface 78.

Figure 4:
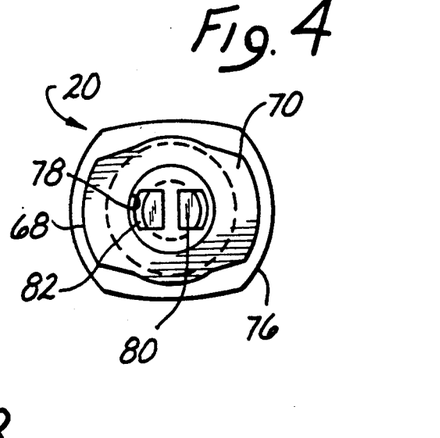
FIG. 4 is an end view of an adhesive spray fitting, as seen generally along the line 4—4 of FIG. 2.
Figure 8:
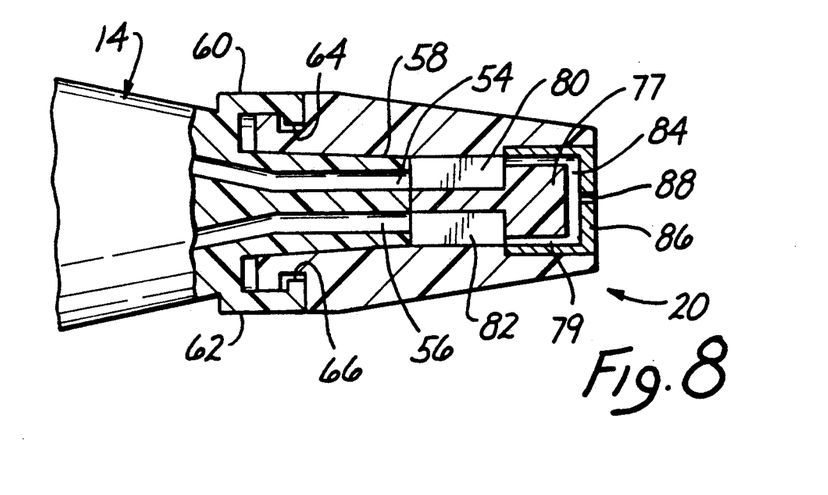
FIG. 8 is an enlarged section through the adhesive spray fitting, shown in exploded position in FIG. 2.

Rather than delivering the mixed adhesive by needle, sometimes it is desirable to spray the mixed adhesive on a surface. This is achieved by spray assembly 20 which has a body 76. The body 76 has a conical interior surface 78, seen in FIG. 2, which meets and seals with the conical nose 58, as shown in FIG. 8. As seen in FIG. 4, ears 68 and 70 are formed on the body and are sized to pass between the collar segments 60 and 62, as previously described, and upon rotation of the body 76 locked behind the flanges 64 and 66. Spray assembly body 76 has separate passages 80 and 82 which respectively align with channels 54 and 56 when the spray assembly body is locked in place, as shown in FIG. 8. The locking structure aligns the passages with the channel to assure passage continuity. The passages 80 and 82 open into space 84 where the fluids are mixed. The space 84 is covered by spray nozzle 86 which has a spray outlet 88. The mixed fluid sprays out of outlet 88 to be applied to the selected surface.

It is critical that the needle assembly or the spray assembly, whichever is selected, be detachably locked to the manifold. It must be detachable so that it may be changed, and locked on so that it cannot become inadvertently driven off. For example, after one use of the biological syringe system with the needle assembly in place, the mixed fluid remains within the needle 74. If the system is returned to use before the tissue adhesive sets up within the needle, it can be reused, but if the adhesive sets up in the needle, the needle must be changed. In the interim condition, if the user attempts to use it and builds up pressure against the plugged-up or almost plugged-up needle, the needle assembly can be ejected. Such is undesirable. Therefore, the needle locking system onto the manifold is critical. It is also critical to lock the spray assembly in place, and it is selected because the biological adhesive also mixes within the spray assembly. Ejection of the spray assembly is not as dangerous, but a loose piece in an operating field is to be avoided.

The locking of the manifold onto the syringes maintains the conical seal so that the biological fluid cannot escape. In the previous condition of plug-up of the needle assembly or spray assembly, actuation of the syringe plungers builds up pressure and could drive the manifold, at least loose and possibly separate from the syringes. When loose, biological fluid escapes, to the detriment of the field, and if the manifold comes loose, it is also a detriment to the field.

Figures 9, 10:
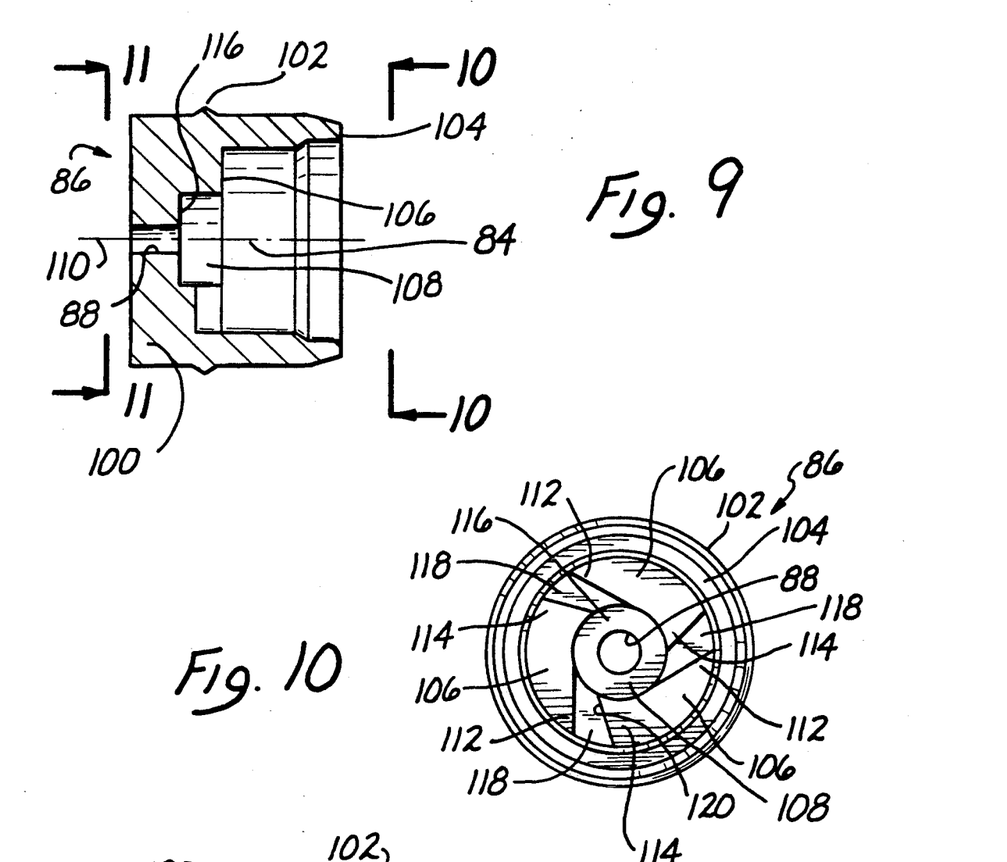
FIG. 9 is a longitudinal cross-sectional view of the spray nozzle of the invention.
FIG. 10 is an elevational view of the spray nozzle of FIG. 9 as seen through section lines 10—10.
Figure 11:
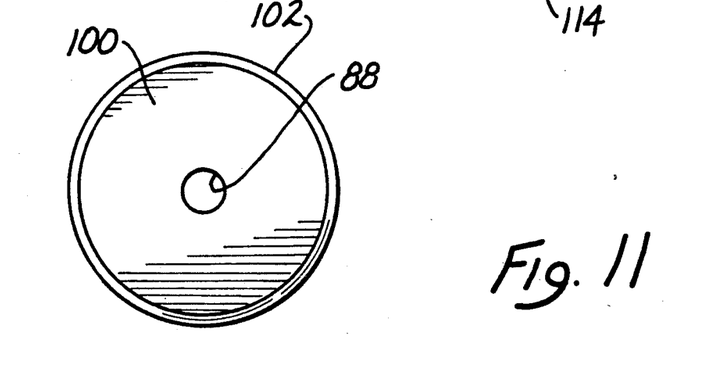
FIG. 11 is an elevational view of the spray nozzle of FIG. 9 as seen through section lines 11—11.

The spraying mechanism of the invention is illustrated in FIGS. 9-11 where spray nozzle 86 is depicted in greater detail. Turning to FIG. 9, the spray nozzle generally denoted by reference numeral 86, is comprised of a generally hollow cylindrical body or cup 100. Body 100 has a circumferential rib 102 defined on its exterior surface which provides for a degree of locking engagement when nozzle 86 is disposed within mixing space 84 as depicted in FIG. 8. The right circumferential end of body 100 as seen in FIG. 9 is radially reduced on both of its outside and inside surfaces to form a tapered edge 104 arranged and configured to fit within a corresponding or conforming surface defined within body 76 of the discharge assembly. The left end of body 100 as shown in FIG. 9 is depicted in elevational view in FIG. 11 and provides a simple flat surface within axially centered spray outlet 88 which is approximately 0.020 inch in diameter.

The interior structure of body 100 is characterized by three inclined symmetrical disposed surfaces 106, best depicted in the elevational view of FIG. 10, but also depicted in cross-sectional view in FIG. 9.

Turning to FIG. 10, the interior structure of spray nozzle 86 is characterized by axial spray outlet 88. A small cylindrical final mixing space 108 is axially disposed about the central axis 110 of the spray nozzle 86 and behind or to the right of spray outlet 88 as depicted in FIG. 9. The diameter of final mixing space 108 is approximately 0.065 inch. Adjacent and symmetrically surrounding final mixing space 108 are three inclined wedged surfaces 106 best depicted in FIG. 10. Each surface 106 is inclined beginning with a high point or thickened portion at region 112 and thereafter sloping downwardly in the depiction of FIG. 10 or, to the left in the depiction of FIG. 9, to a low or thinned portion 114. In the illustrated embodiment, the dimension of the thick or high portion 112 is approximately 0.030 inch with the thin portion 114 approaching or merging into the basal level of surface 116 best depicted in FIG. 9.

Each inclined surface 106 is separated by a channel 118 which is generally coplanar with surface 116. As depicted in FIG. 10, the angled sides 120 of each wedge 106 forms an angle 122 of approximately 15 degrees relative to a radius of spray nozzle 86.

Body 76 of the discharge assembly includes a solid cylindrical extension 77 best depicted in FIG. 2 which extends into the mixing space 84 and is axially aligned with longitudinal axis 110 of spray nozzle 86. Therefore, nozzle 86 and cylindrical portion 77 form a small annular cylindrical space 79 into which the two fluids from passages 54 and 80 on one hand, and 56 and 82 on the other, flow as best depicted in FIG. 8. The two fluids mix only to a limited degree in annular space 79 along the interface between the two streams as the streams spread into the two longitudinal halves of the cylindrical annular space 79. No substantial mixing occurs until the fluids reach mixing space 84 which is a disk-shaped space between nozzle 76 and cylinder 77 which is approximately 0.110-0.115 inch in height and 0.070-080 inch in diameter. Therefore, cylindrical annular space 79 can be visualized as a cylindrical shell approximately 0.020-0.030 inch in thickness, approximately 0.110-0.115 inch in height and approximately 0.132 inch in outer diameter. Space 79 communicates with mixing space 84 which can be visualized as a disk-shaped space approximately) 0.040 inch in height and 0.132 inch in diameter.

At this point, the fluid of each half impinges upon the uppermost or thick portion 112 of surfaces 106 defined on the internal structure of nozzle 76. The fluid is then given a rotary motion as it flows from the high point 112 of each wedge surface 106 to low point 114. Substantial mixing occurs during this portion of the fluid's travel.

Once the fluid reaches low point 114 of each surface 106 it is delivered to the adjacent channel 118. The fluid flow then changes abruptly due to the high wall presented by surface 120 and is directed radially inward along channel 118.

The flow exits channel 118 into final mixing space 108 in a generally tangential direction with respect to longitudinal axis 110. The mixed fluid becomes even more thoroughly mixed as it is swirled or rotated rapidly in a clockwise motion as shown in FIG. 10 within final mixing space 108. The mixed fluid tends to flow from the outer periphery of cylindrical mixing space 108 towards spray orifice 88 where it is ejected under pressure.

The ejected fluid continues its rotary motion even after being ejected, which assists in atomizing the mixed fluids to provide a more thoroughly distributed and homogeneous application across the area of the wound.

This invention has been disclosed in its most preferred embodiment, and it is clear that it is susceptible to numerous modifications and embodiments within the ability of those skilled in the art and without the exercise of the inventive faculty. Accordingly, the scope of this invention is defined by the scope of the following claims.

We claim:

1. A biological syringe system for delivering a first and second fluid in a mixed composition comprising:
    a manifold, said manifold having first and second component channels therethrough, said manifold further having first and second input connections respectively communicating with said first and second component channels, said first and second component channels terminating in exit channels adjacent to each other on an opposing end of said manifold;
    a discharge assembly coupled to said opposing end of said manifold and receiving fluid from both of said exit channels, said discharge assembly for mixing fluid from both of said exit channels and delivering said mixed fluid in a spray, said discharge assembly having a first and second passage therethrough communicating with said exit channels from said manifold for carrying fluid from said first and second component channels in corresponding first and second passages within said discharge assembly while maintaining said first and second fluids separated from each other, said discharge assembly having a mixing space defined therein to receive separate flows from said passages, said discharge assembly further comprising mixing means disposed within said mixing space to thoroughly mix said first and second fluids for the first time within said mixing space and to immediately thereafter atomize said thoroughly mixed first and second fluids in a spray discharged from said discharge assembly.

2. The biological syringe system of claim 1 wherein said means for thoroughly mixing and atomizing said first and second fluid into a spray comprises a shaped spray nozzle having a spray outlet defined therein, said shaped spray nozzle being disposed within said mixing space.

3. The biological syringe system of claim 2 wherein said first and second passages have outlet ends, and wherein said discharge assembly comprises a solid cylindrical body disposed within said mixing space, said solid cylindrical body having a first end surface adjacent outlet ends of said first and second passage in said discharge assembly, said first and second fluids exiting said outlet ends of said passages and flowing into a cylindrical annular space between said nozzle disposed in said mixing space and said cylindrical body disposed in said mixing space, said first and second fluids mixing for the first time within said cylindrical annular space and flowing to a portion of said mixing space adjacent an opposing end of said solid cylindrical body opposite said spray outlet, said mixed first and second fluids then being expressed through said spray outlet as atomized spray particles.

4. The syringe system of claim 3 comprising means for swirling said first and second fluids together in said mixing space.

5. A biological syringe system for delivering a first and second fluid in a mixed composition comprising:
    a manifold, said manifold having first and second component channels therethrough, and further having first and second input connections respectively communicating with said first and second component channels, said first and second component channels terminating in exit channels adjacent to each other on an opposing end of said manifold;
    a discharge assembly coupled to said opposing end of said manifold and receiving fluid from both of said exit channels, said discharge assembly for mixing fluid from both of said exit channels and delivering said mixed fluid in a spray, said discharge assembly having a first and second passage therethrough communicating with said exit channels from said manifold for carrying fluid from said first and second component channels in corresponding first and second passages within said discharge assembly while maintaining said first and second fluids separated from each other, said first and second passages having outlets ends, said discharge assembly having a mixing space defined therein to receive separate flows from said passages, said discharge assembly further comprising a shaped spray nozzle having a spray outlet defined therein, said shaped spray nozzle being disposed within said mixing space to thoroughly mix said first and second fluids for the first time within said mixing space and to immediately thereafter atomize said thoroughly mixed first and second fluids in a spray discharged from said discharge assembly; said discharge assembly comprising a solid cylindrical body disposed within said mixing space, said solid cylindrical body having a first end surface adjacent outlet ends of said first and second passage in said discharge assembly, said first and second fluids exiting said outlet ends of said passages and flowing into a cylindrical annular space between said nozzle disposed in said mixing space and said cylindrical body disposed in said mixing space;
    swirling means for swirling said first and second fluids together in said mixing space, said first and second fluids mixing for the first time within said cylindrical annular space and flowing to a portion of said mixing space adjacent an opposing end of said solid cylindrical body opposite said spray outlet, said mixed first and second fluids then being expressed through said spray outlet as atomized spray particles; and a plurality of wedged shaped surfaces azimuthally disposed about said spray outlet, said wedged shaped surfaces being inclined in an azimuthal direction relative to said spray outlet to impel an azimuthal flow to said first and second fluids about said spray outlet.

6. The syringe system of claim 5 wherein a generally radially disposed channel separates each of said wedged shaped surfaces, said channel in combination with an adjacent wedged shaped surface directing flow of said first and second fluid in an azimuthal direction about a predetermined cylindrical space adjacent to and centered about said spray outlet.

7. The syringe system of claim 4 wherein said means spirals said first and second fluids together to thoroughly mix said first and second fluids for the first time immediately prior to ejection through said spray outlet.

8. A method for applying a tissue adhesive and protective covering which chemically forms and hardens as applied comprising the steps of:
providing a first fluid;
providing a second fluid which when mixed with said first fluid hardens into said tissue adhesive;
forcing said first and second fluids from a corresponding first and second syringe into corresponding first and second passages;
partially mixing said first and second fluids together by flowing said fluids under pressure within a cylindrical annular space; and
forcing said partially mixed first and second fluids from said cylindrical annular space into a final mixing chamber;
thoroughly mixing said first and second fluids in said final mixing chamber;
forcing said thoroughly mixed fluids to an axial spray orifice;
atomizing said thoroughly mixed first and second fluids by pressured ejection of said fluids through said spray orifice at a predetermined minimum pressure,
whereby mixture of said first and second fluids is substantially improved, strength and hardening of said tissue adhesive substantially improved, and wherein thorough mixing occurs just prior to application in atomized form.

9. The method of claim 8 wherein said first and second fluids are swirled together as said first and second fluid flows from said outlet ends of said passages through said cylindrical annular space and thence radially inward to an axial spray orifice to thoroughly mix said fluids within a mixing space of predetermined limited volume followed by immediate ejection in atomized form for application and hardening.

10. The method of claim 8 where in said step of thoroughly mixing said first and second fluids, said first and second fluids are spiralled together for the first time just prior to forcing said fluids through said spray outlet.

11. A method for applying a tissue adhesive and protective covering which chemically forms and hardens as applied comprising the steps of:
providing a first fluid;
separately providing a second fluid which when mixed with said first fluid hardens into said tissue adhesive;
maintaining said first and second fluids substantially separate as said fluids are delivered to a mixing chamber;
thoroughly mixing said first and second fluids in said mixing chamber for the first time;
atomizing said thoroughly mixed first and second fluids by pressured ejection of said fluids through a spray orifice at a predetermined minimum pressure, said step of thoroughly mixing being performed immediately before said step of atomizing so that substantially no reaction has occured between said first and second fluids until after said step of atomizing,
whereby mixture of said first and second fluids is substantially improved, strength and hardening of said tissue adhesive substantially improved, and wherein thorough mixing occurs just prior to application in atomized form.

12. The method of claim 11 where said step of thoroughly mixing said first and second fluids comprises the step of swirling said first and second fluids together for the first time in said mixing chamber just prior to atomizing.

13. The method of claim 11 where said step of thoroughly mixing is performed relative to said other steps of said method to minimize the time during which said first and second fluids are being mixed together.

14. The method of claim 13 further comprising the step of uniformly applying said atomized mixture of said first and second fluids to a selected wound site.

15. The method of claim 14 further comprising the step of curing said applied mixture of said first and second fluids to form an artificial tissue surface.

16. The method of claim 15 where said step of curing is performed to minimize the time during which curing of said artificial tissue occurs after said step of atomizing.

17. A method for applying a tissue adhesive and protective covering which chemically forms and hardens as applied comprising the steps of:
providing a first fluid;
providing a second fluid which when mixed with said first fluid hardens into said tissue adhesive;
forcing said first and second fluids from a corresponding first and second syringe into corresponding first and second passages;
partially mixing said first and second fluids together by flowing said fluids under pressure within a cylindrical annular space;
forcing said partially mixed first and second fluids from said cylindrical annular space into a final mixing chamber;
thoroughly mixing said first and second fluids in said final mixing chamber; and
forcing said thoroughly mixed fluids to an axial spray orifice to atomize said thoroughly mixed first and second fluids by pressured ejection of said through said spray orifice at a predetermined minimum pressure,
wherein said step of mixing said first and second fluids are swirled together as said first and second fluid flows from said outlet ends of said passages through said cylindrical annular space and thence radially inward to an axial spray orifice to thoroughly mix said fluids within a mixing space of predetermined limited volume followed by immediate ejection in atomized form for application and hardening, whereby mixture of said first and second fluids is substantially improved, strength and hardening of said tissue adhesive substantially improved and wherein thorough mixing occurs just prior to application in atomized form.

18. An apparatus for applying a tissue adhesive and protective covering which chemically forms and hardens as applied comprising:

first fluid providing means for providing a first fluid to a mixing area within said apparatus;

second fluid providing means for providing to said mixing area a second fluid which when mixed with said first fluid hardens into said tissue adhesive;

mixing means for thoroughly mixing said first and second fluids within said mixing area;

atomizing means for atomizing said thoroughly mixed first and second fluids by pressurized ejection of said fluids from said mixing area; and locking means for securely locking said mixing means and said atomizing means to said first fluid providing means and said second fluid providing means during pressurization of said first and second fluids, whereby said apparatus for applying a tissue adhesive and productive covering remains safely locked together as an integral unit even should said first and second fluids become coagulated into a solid mass within said means for mixing and atomizing.

19. The apparatus of claim 18 wherein said means for providing said first and second fluid comprises a first and second syringe respectively for holding said first and second fluids and a corresponding first and second plunger for forcing said first and second fluids from said first and second syringes respectively, a manifold having first and second corresponding component channels therethrough and first and second input connections respectively communicating with said first and second component channels, said first and second component channels terminating at corresponding exit channels adjacent to each other on opposing ends of said manifold; and wherein said means for thoroughly mixing and atomizing said first and second fluids comprises a discharge assembly coupled to said opposing end of said manifold and receiving fluid from both said exit channels said discharge assembly from mixing fluid from both the said exit channels and delivering said mixed fluid in a spray, said discharge assembly having a first and second passage there through communicating with said exit channels from said manifold for carrying fluid from said first and second component channels in corresponding first and second passages within said discharge assembly while maintaining said first and second fluids separated from each other, said discharge assembly having a mixing space defined therein to receive separate flows from said passages, said discharge assembly further comprising mixing means disposed within said mixing space to thoroughly mix said first and second fluids for a first time within said mixing space and to immediately thereafter atomize said thoroughly mixed said first and second fluids in a spray discharged from said discharge assembly; and wherein said locking means comprises a Luer lock coupling said manifold to said first and second syringes and a Luer lock coupling said discharge assembly to said manifold, so that even though said first and second fluids may coagulate within said discharge assembly, exertion of pressure on said first and second fluids from said first and second plunger will not cause said biological syringe system to decouple at any component part.

* * * * *

UNITED STATES PATENT AND TRADEMARK OFFICE
CERTIFICATE OF CORRECTION

PATENT NO. : 5,116,315
DATED      : May 26, 1992
INVENTOR(S) : Emil E. Capozzi; H. Stephen Cooksten It is certified that error appears in the above-identified patent and that said Letters Patent is hereby corrected as shown below:

On title page, item [54], should read as follows:

Inventors:  Emil E. Capozzi, Costa Mesa;

H. Stephen Cookston, Malibu, both of Calif.

Signed and Sealed this

Sixteenth Day of November, 1993

Attest:

BRUCE LEHMAN

Attesting Officer

Commissioner of Patents and Trademarks